United States Patent [19]

Citrin

[11] 4,358,203
[45] Nov. 9, 1982

[54] APPARATUS FOR ANALYZING AND EVALUATING TESTS IN A PLURALITY OF WELLS

[75] Inventor: Paul S. Citrin, Danbury, Conn.

[73] Assignee: Becton Dickinson and Company, Paramus, N.J.

[21] Appl. No.: 214,998

[22] Filed: Dec. 10, 1980

[51] Int. Cl.³ .................... C12Q 1/00; G01D 9/00
[52] U.S. Cl. .................... 356/432; 346/33 A; 346/104; 435/33; 435/34; 435/287
[58] Field of Search .......... 356/432, 440; 346/33 A, 346/78, 104; 435/32, 33, 34, 38, 287, 291

[56] References Cited

U.S. PATENT DOCUMENTS

| | | | |
|---|---|---|---|
| 3,614,241 | 6/1971 | Sanford | 346/33 A |
| 3,936,356 | 2/1976 | Janin | 435/34 |
| 4,116,565 | 9/1978 | Powell et al. | 346/33 A |
| 4,130,824 | 12/1978 | Amos et al. | 346/33 A |

Primary Examiner—R. A. Rosenberger

[57] ABSTRACT

An apparatus is described with which a plurality of microbiological tests made in wells located in a pattern of rows on a tray can be conveniently analyzed and evaluated. A housing is formed with a tray analysis section and over which an arm is mounted to move from row to row. A plurality of manually activated signal generators are mounted on the arm, with the generators being aligned with a well in a row to enable the operator, upon identification of a particular well in a row as representative of analysis, to actuate the signal generator in registration therewith. The signals are representative of a score value and are recorded on score forms located in a test scoring section over which the arm moves with recording elements, also mounted on the arm. An elongated illuminator for a row of wells is described and which is conveniently adjusted to view selected test wells against different background lighting. The apparatus is particularly effective in color analysis of test wells by use of an apertured mask having color markings adjacent corresponding well locations.

29 Claims, 12 Drawing Figures

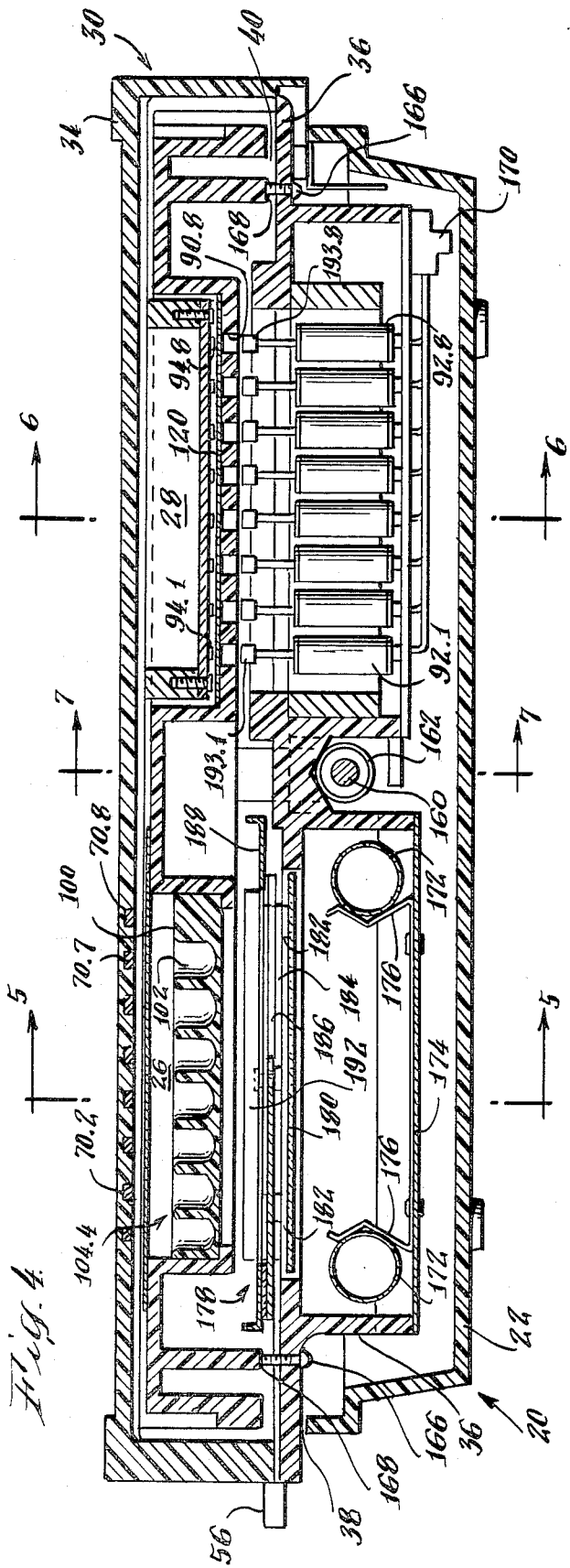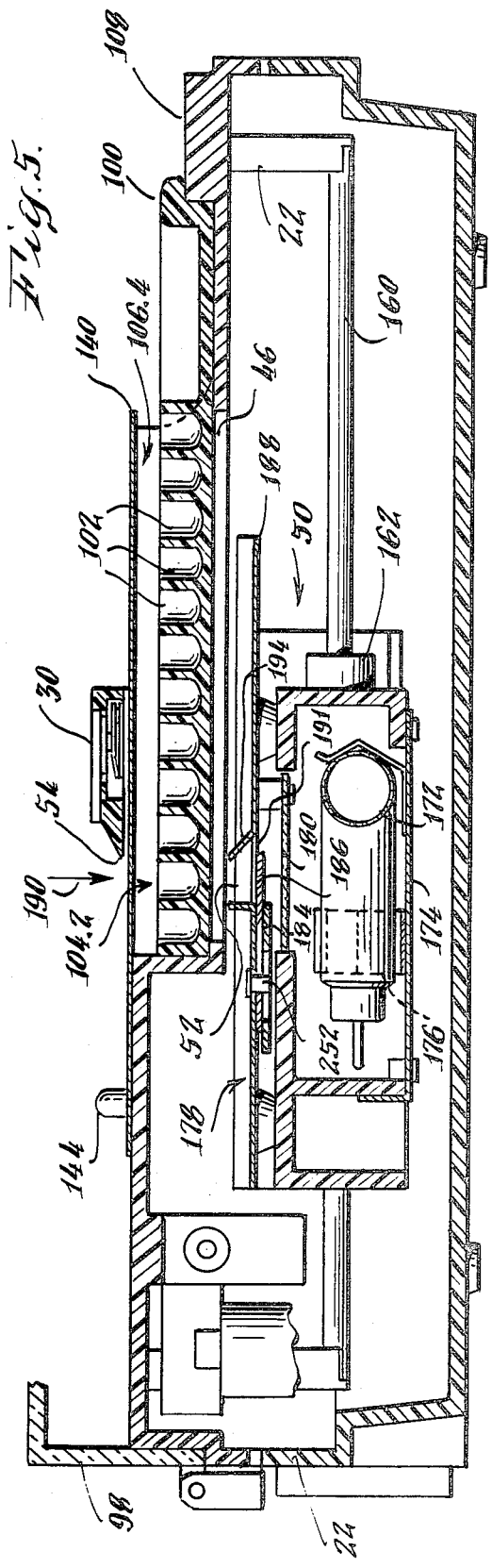

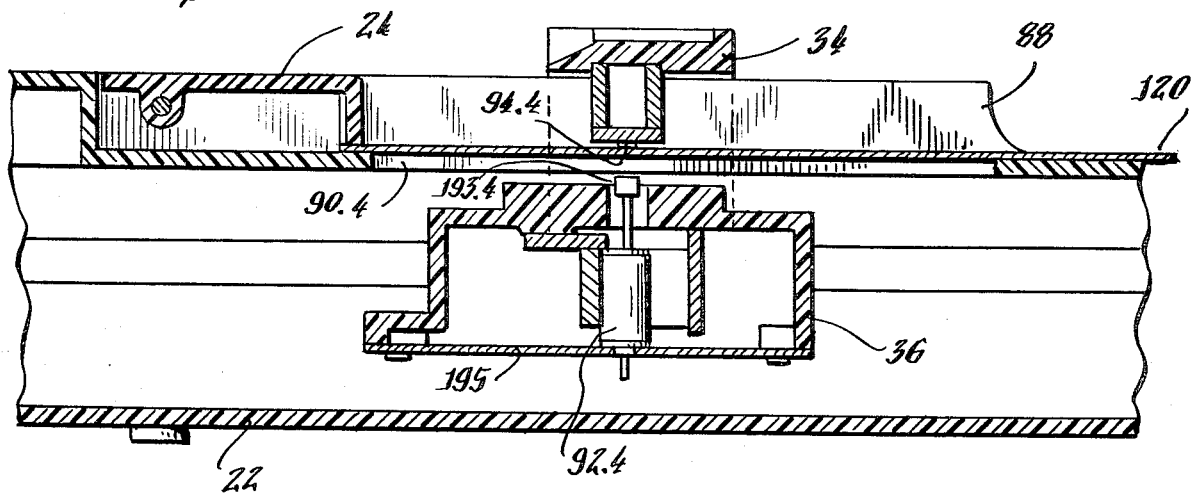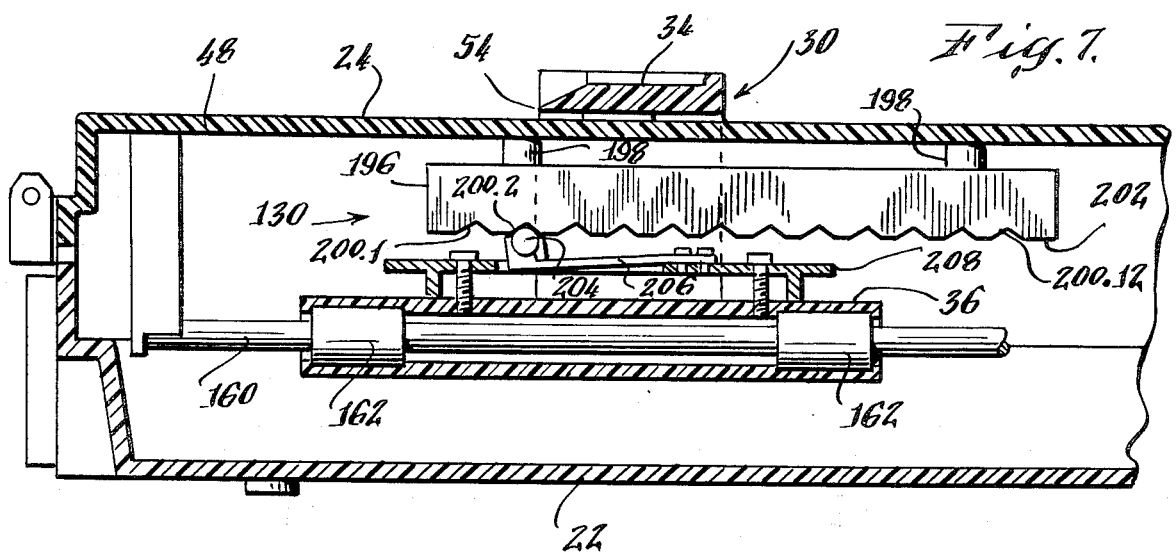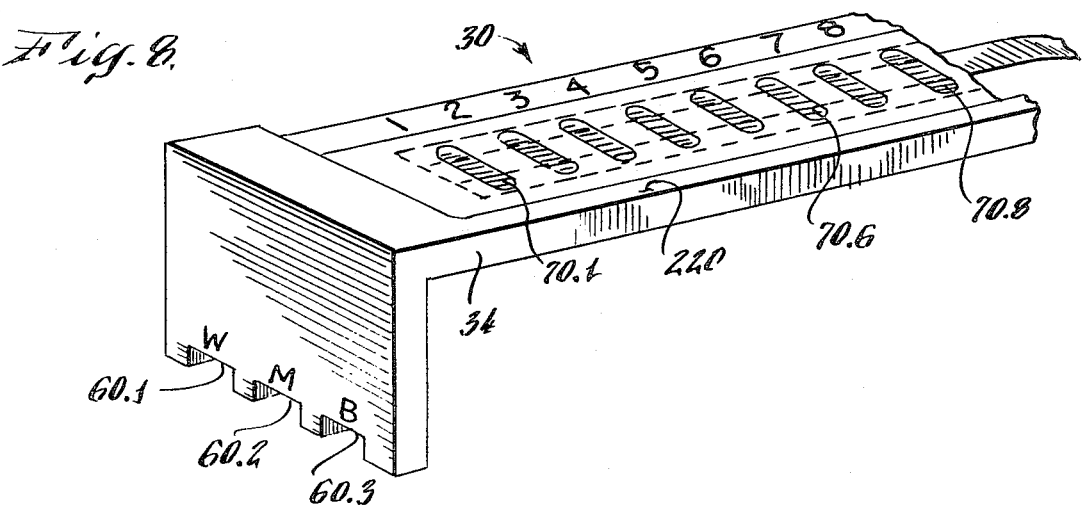

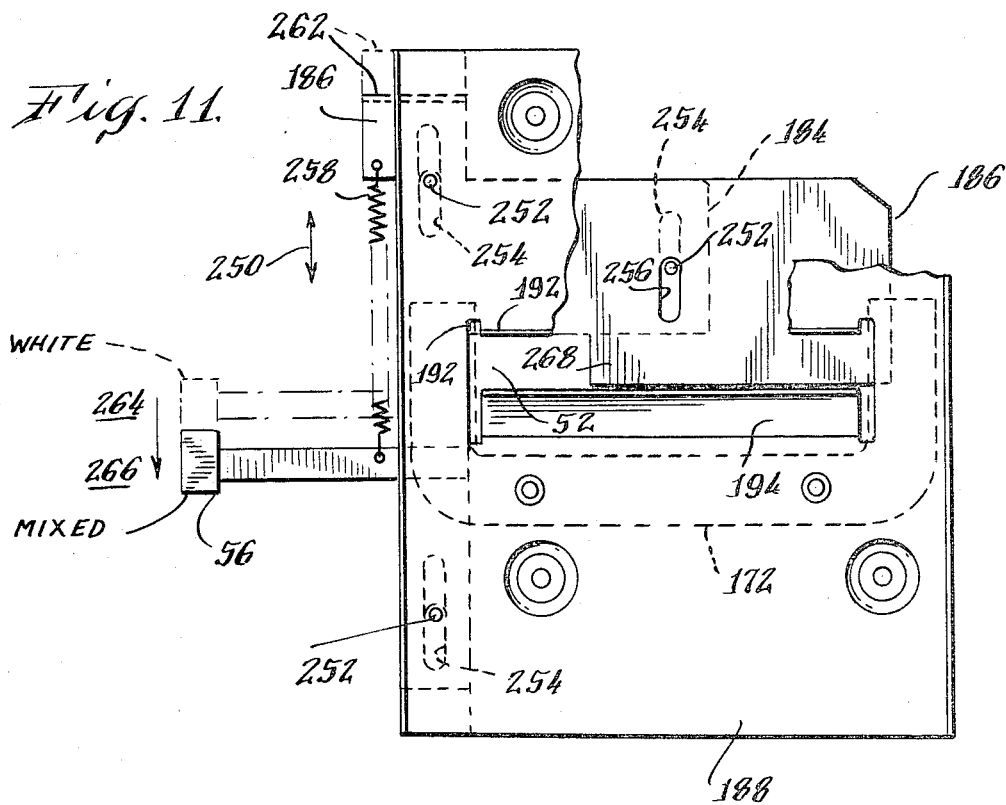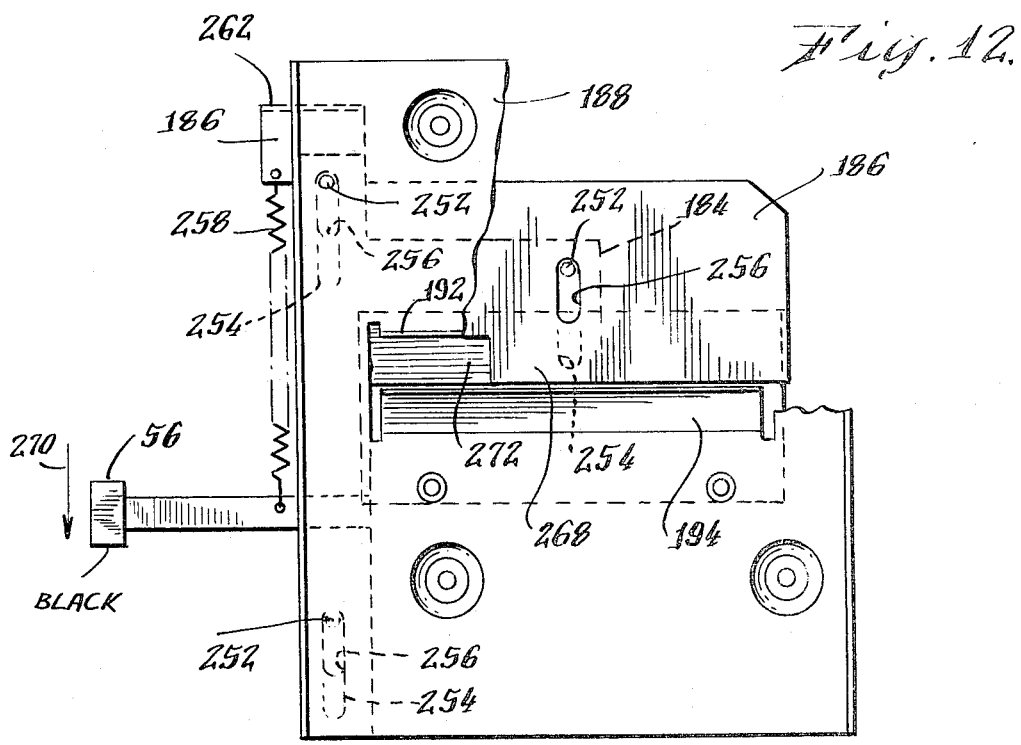

APPARATUS FOR ANALYZING AND EVALUATING TESTS IN A PLURALITY OF WELLS

FIELD OF THE INVENTION

This invention relates to an apparatus for visual analysis of tests such as turbidometric and/or colorimetric tests. More specifically, this invention relates to an apparatus for analyzing and evaluating microbiological tests made in a plurality of wells located in a tray.

BACKGROUND OF THE INVENTION

Microbiological tests for the identification and/or counting of organisms have been developed. Such tests are commonly performed in laboratories in hospitals and medical clinics and the like. In one such known test, a minimum inhibiting concentration (MIC) is obtained by exposing an organism to different dilutions of an antibiotic and analyzing which dilution level is sufficient to kill and/or inhibit growth the organism.

Such MIC test is commonly done in a tray containing a regular pattern of small wells usually arranged in rows and columns. In one such tray, for example, there may be twelve rows and seven columns of wells for a total of 84 wells. Other trays may have a different number of wells. Each row of wells may contain different antibiotic in dilutions which are typically graded with scores in levels of the power of two, e.g. 1, 2, 4, 8, 16, 32 and 64, or some other sequence of numbers.

A technician commences such MIC test by employing a tray in which the wells contain antibiotics with progressive concentrations and then adds a growth solution containing the organism in each of the wells. After an incubation period, the technician visually analyzes the wells to determine at which antibiotic concentration (the MIC) the organism appears to have been killed and/or growth inhibited. This analysis is done visually by scanning a row of wells containing a particular antibiotic and noting in which well the solution appears, for example, cloudy, opaque or clear. The technician does this analysis for each row and assigns a score value to his analysis by noting on a corresponding form carrying score value notations which well in the row contained the minimum inhibitory concentration.

The trays of wells usually are transparent so that the technician may observe the test wells against a light or dark background. In other microbiological tests the tray may include in some of the wells various components which, when innoculated with the specimen solution, react with certain organisms in a particular manner. These wells, when analyzed and appropriately evaluated by the technician, provide an identification of the organism.

In a typical laboratory environment a large number of such organism analyses must be performed. This often results in a fatigue of the technician who has to constantly look at tiny test wells and becomes prone to note the wrong score value on the score form and would welcome a procedure which would simplify the analysis and evaluation with less chance for error and with greater speed.

SUMMARY OF THE INVENTION

With an apparatus in accordance with the invention, the analysis and evaluation of tests made in a plurality of wells arranged in a pattern of rows on a tray can be made accurately and conveniently. As described herein with reference to one form for an apparatus in accordance with the invention, a housing is provided with its top surface formed into a test analysis section sized to receive a tray having a plurality of test containing wells. An arm is mounted to the housing to move over its top surface and align a reference edge of the arm along rows of wells. The arm carries a plurality of score signal generators which are respectively located for visual registration with a different well in a row of wells of a tray placed in the test analysis section.

As the arm is moved across the top surface of the housing and the arm's reference edge is successively aligned with a row of test wells, the technician makes a visual analysis of the tests and selects a well in the row by actuating a score signal generator which is in registration with the selected well. The score signals associated with the various rows then conveniently represent an evaluation of the tests in the rows and may be used to make a record of the analysis. The record may be a visual notation on a form or stored in a magnetic medium or the memory of a signal processor.

With an apparatus in accordance with the invention, a tray carrying a plurality of microbiological test wells can be accurately and conveniently analyzed and evaluated. As described herein for one form of the invention, an apparatus is provided with a tray receiving section and arm as described and also a test scoring section shaped to receive a score form. The score form has score value notations located thereon in corresponding spatial relationship with the location of wells on a tray. The score value locations are so spaced that as the reference edge of the arm is aligned with rows of test wells, a corresponding row of score value locations is spaced below the arm and operatively aligned with actuators for producing a visual notation in response to a score signal.

A rapid and accurate analysis of a tray of test wells can be conveniently made while their evaluation can be simultaneously accurately recorded as the arm is moved to successive positions aligned with a row of wells on a tray. The technician's access to score signal generators is visually effective to accurately identify each well representative of the analysis, while simultaneously and accurately obtaining a physical record of the analysis.

The arm is provided as described for a preferred form of the invention, with a row of recording elements which are so aligned with the score signal generators as to mark a notation on the score form at the proper location. An adjustable shutter assembly is mounted to the arm to move therewith inside the housing below the top surface. The shutter assembly is located below the tray receiving section to control background illumination for a group of wells in a tray depending upon the type of background light needed for a visual analysis of the tests in the wells.

The arm has a closed loop shape composed of upper and lower segments located respectively above and below the top surface of the housing. The upper arm segment serves to provide an accurate visual reference edge for alignment of the arm with a row of wells as well as carry manually actuated score signal generators. The lower arm segment supports the background shutter assembly, electrical controls and actuators for producing the markings on a score form in response to a score signal.

With such arm construction, the upper segment overlying the housing with the tray analysis and test scoring sections contributes with its shape, its alignment with test wells and convenience in generating score signals to a more consistent accuracy in the analysis and evaluation by a technician.

Such improvement in the analysis of test wells can be particularly appreciated when a visual color analysis of test wells is required. In such case as described herein for one form of the invention, a mask is provided to overly the tray analysis section but below the arm. The mask has a transparent section, such as formed by a cut-away aperture, and which is shaped to visually reveal certain wells of an underlying tray. On the mask and adjacent the transparent section are color indications to aid the technician in the visual color identification of the tests in adjacently located wells. Score signals are generated as a result of the technician's analysis of the test well whose color most closely matches a particular color value. As further described herein, the shutter assembly is shaped to provide the desired background illumination below the test wells to enhance such color identification.

It is, therefore, an object of the invention to provide an apparatus for analyzing and evaluating test wells arranged in rows in a tray. It is a further object of the invention to provide such apparatus which is convenient to use, enhances the accuracy of the visual analysis and conveniently provides score signals representative of an evaluation of the visual analysis. It is a still further object of the invention to provide an apparatus with which the analysis of microbiological tests performed in a plurality of wells in a tray can be conveniently analyzed and accurately evaluated.

These and other objects and advantages of the invention can be understood from the following description of a test analysis and evaluating apparatus described in conjunction with the drawings.

BRIEF DESCRIPTION OF DRAWINGS

FIG. 4 is a section view of the apparatus as shown in FIG. 2 and taken along the line 4—4 therein;

FIG. 5 is a section view of the apparatus as shown in FIG. 2 and taken along the lines 5—5 in FIG. 4;

FIG. 6 is a partial section view of the apparatus as shown in FIG. 2 and taken along the lines 6—6 in FIG. 4;

FIG. 7 is a partial section view of the apparatus as shown in FIG. 2 and taken along the lines 7—7 in FIG. 2;

FIG. 8 is a partial perspective view of an upper segment of an arm employed in an apparatus in accordance with the invention;

FIGS. 11 and 12 are broken-away top plan views of the assembled shutter assembly shown in FIG. 10.

DETAILED DESCRIPTION OF DRAWINGS

Figure 1:
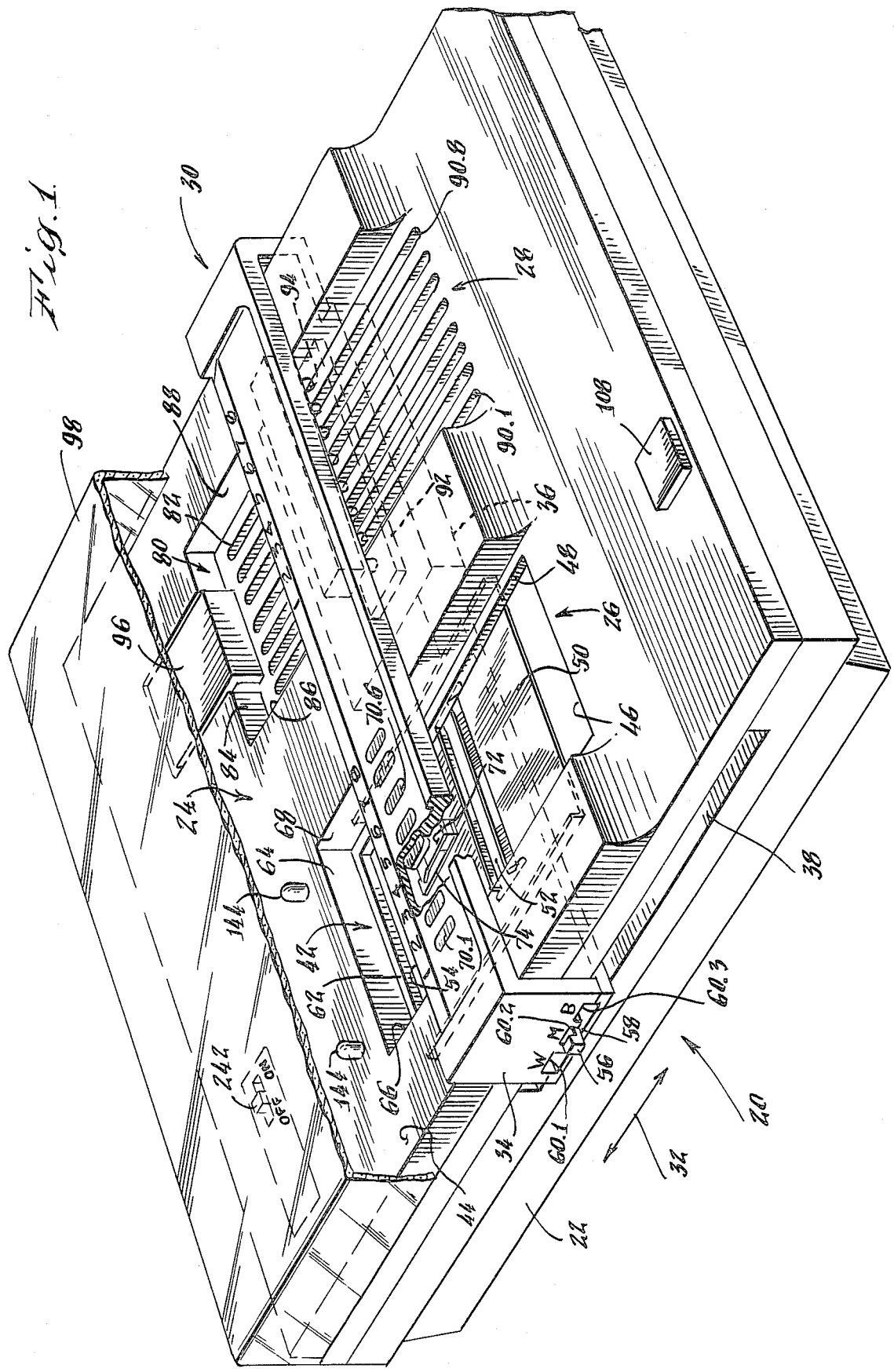
FIG. 1 is a perspective partially broken away view of an apparatus in accordance with the invention.

With reference to FIG. 1, an apparatus 20 in accordance with the invention is shown formed of a housing 22 with a top surface 24 formed into a test analysis section 26 and a test scoring section 28.

An arm 30 is shown spaced from and suspended over top surface 24 and is supported inside housing 22 for movement along the top surface 24 in the direction indicated by arrow 32. The arm 30 is formed of an upper segment 34 and lower segment 36 located inside housing 22. The arm is supported inside housing 22 and extends through slots 38, 40 (only one slot being visible in the view of FIG. 1).

The test analysis section 26 is formed in a recess 42 below a platform 44 of top surface 24 and is sized to receive a tray containing a plurality of wells arranged in rows and columns as will be further explained. The test section has an extended aperture 46 in the wall 48 of top surface 24 and reveals a test well illuminating and shutter assembly 50 mounted to the lower segment 36 of arm 30. The assembly 50 provides a controlled illumination of a group of test wells through a slot 52 aligned below and in front of a reference edge 54 of upper segment 34 of arm 30.

Control over the background of slot 52 and thus a row of wells is provided with a shutter lever 56 which laterally extends through a slot 58 in arm 30. The shutter lever 56 is formed of a spring element biased to move into either of three control notches 60.1, 60.2 and 60.3, respectively representative of a white, mixed, or all black background.

Recess 42 has a bottom wall 62 surrounding aperture 46 to support a tray which seats against an end wall 64 and freely fits, but with little clearance, between side walls 66, 68. End wall 64 is so located that reference edge 54 on arm 30 may be moved to successive indent positions in alignment with rows of wells on a tray.

Arm 30 is provided with a plurality of score signal generators 70 in the form of push button switches. The switches 70 are shown in the view of FIG. 1 as formed of a pair of spring conductors 72, 74, the upper 72 of which may be depressed by an operator. Preferably, switches 70 are of membrane form as will be further described with reference to FIGS. 8 and 9. Switches 70 are spaced on arm 30 in a predetermined manner for registration with a well in a row of wells in a tray and when actuated, generate a score signal representative of an evaluation of a visual analysis of test wells located in the test analysis section 26.

The test scoring section 28 is formed with a recess 80 having a bottom 82, end wall 84 and side walls 86, 88. Bottom 82 has a plurality of longitudinal parallel slots 90 sized to receive from inside housing and below bottom 82 arm mounted recording elements 92 for making a notation on a score form in coooperation with anvils 94 mounted to arm 30 over test scoring section 28. The shape of the notation may vary as desired, depending upon the shape of anvil 94. Thus an arrow, dot, dash or other mark may be used and is placed adjacent a printed score value to indicate the analysis and evaluation made by the technician of the corresponding row of test wells 104.

A spring loaded, pivotly mounted retainer 96 is shown located near end wall 84 to maintain a score form in registration with the test analysis section. A pivotly mounted cover 98 is provided to protect internal devices in the housing 22.

With the arm 30 being movable over the housing top surface 24, a technician may conveniently align the arm with successive rows of wells for analysis and evaluation. This may be particularly appreciated with reference to FIG. 2. In this figure a tray 100 having a plurality of test wells 102 is shown placed in test analysis section 26 below arm 30. The tray 100 is formed of a transparent plastic material and has a total of eighty-four wells 102 arranged in a regular rectangular pattern of twelve rows 104 and seven columns 106.

Although the use of trays with a plurality of test wells is well known for use in microbiological tests, the particular tray 100 and test analysis section 26 are shaped to place the tray 100 with particular alignment relative to arm 30 and test scoring section 28. A tray alignment projection 108 is shown on top surface 24 of housing 22 and aids in precisely locating and retaining a tray 100 in the desired aligned position in test analysis section 26.

With the placement of a tray 100 in test analysis section 26, the well columns 106 are in registration with the score signal generators 70 as shown.

The test scoring section 28 is sized and shaped to receive a score form 120 on which there are rows 122 of score locations 124 respectively in correspondent locations with respect to the rows 104 and individual wells 106 in a tray 100. The spacing between score location rows 122 is made the same as between test well rows 104. In this manner, as the reference edge 54 of arm 30 is aligned just below a row of wells, such as 104.2, the recording elements 92 are in registration with score locations 124 in a row 122.2 on score form 120.

The score form 120 may be a single sheet, but preferably is made up of multiple sheets with identical notations and each sheet provided with an ink carrying material which, upon application of pressure form a print element, will form a character. The score form may have such appearance and carry notations as is appropriate for the type of tests contained in the wells 102 in tray 100. For example, the sixth test well row 104.6 in tray 100 may contain tetracycline in varying concentrations as represented by the score value numbers noted in the corresponding row 122.6 on score form 120. Other test well rows may contain different materials, some of which are noted on the form 120, such as tobramycin, cephalothin, carbenicillin and others which are not indicated to preserve clarity of the drawing.

The score form 120 is so designed that the score locations 124, as denoted by small marks adjacent the concentration numbers, are in registration with the recording elements 92 when the associated row 104 of test wells 102 is aligned with reference edge 54 of arm 30. In the embodiment as shown, this is obtained by sizing form 120 in such manner that when its top edge 126 is in abutment with the end wall, 84, the desired registration is obtained. The distance, d, between end walls 64 and 84 is, therefore, known and selected to provide score form 120 with sufficient space above the first row 122.1 for entry of information such as patient identification, etc. while also enabling use of a straight ruler shape for upper segment 34 of arm 30.

Arm 30 is provided with successive stable index positions, which coincide with the alignment of reference edge 54 with the various rows 104 of wells 102. This is obtained with an indent mechanism 130 (see FIG. 7) operative on the lower segment 36 of arm 30 and inside housing 22.

In the operation of apparatus 20, the technician aligns reference edge 54 just below a row 104 of test wells 102, by which arm 30 is automatically operatively registered with a corresponding row 122.2 of score locations 124 on score form 120. As the technician makes a visual analysis of the wells in row 104.2, the one well 102 representative of a particular test condition, such as a transition from cloudy to clear, is identified and the appropriately registered score signal generating switch 70 actuated. This in turn causes the actuation of a corresponding recording element 92 in test scoring section 28 and thus form a notation on score form 120 at the proper score location 124.

The technician may thus advantageously concentrate his attention to the test analysis section 26 and assure proper registration with the appropriate row 104 of test wells and the visual analysis of that row without concern of the accuracy of the transfer of the visual analysis to the score form 120. This transfer is automatically assured by the actuation of the proper switch, which by its visual registration with a well 102 in a row 104 and close proximity thereto facilitates in a rapid and accurate transfer and thus evaluation of the technician's visual analysis.

Although the spacings between adjacent rows 122 is the same as between test well rows 104 on a tray 100, the lateral spacing between columns of score locations 124 may vary depending upon lateral spacing of recording elements 94 and desired width for forms 120. The lateral edges 128.1 and 128.2 of a score form 120 are preferably closely spaced to side walls 86, 88 of test scoring section 28 while still enabling free clearance fit between the form and the side walls 86, 88.

In the tray 100 there are seven columns 106 of test wells 102, yet there are eight score signal generators, with the extreme right one, 70.8, which is not in registration with any test well 102, being used when, for example, none of the antibiotic concentrations in the row of test wells can be used in the analysis. In such case the score signal generator 70.8 is actuated to correspondingly cause the extreme right recording element 92.8 to record a notation at score location 124.8.

Figure 2:
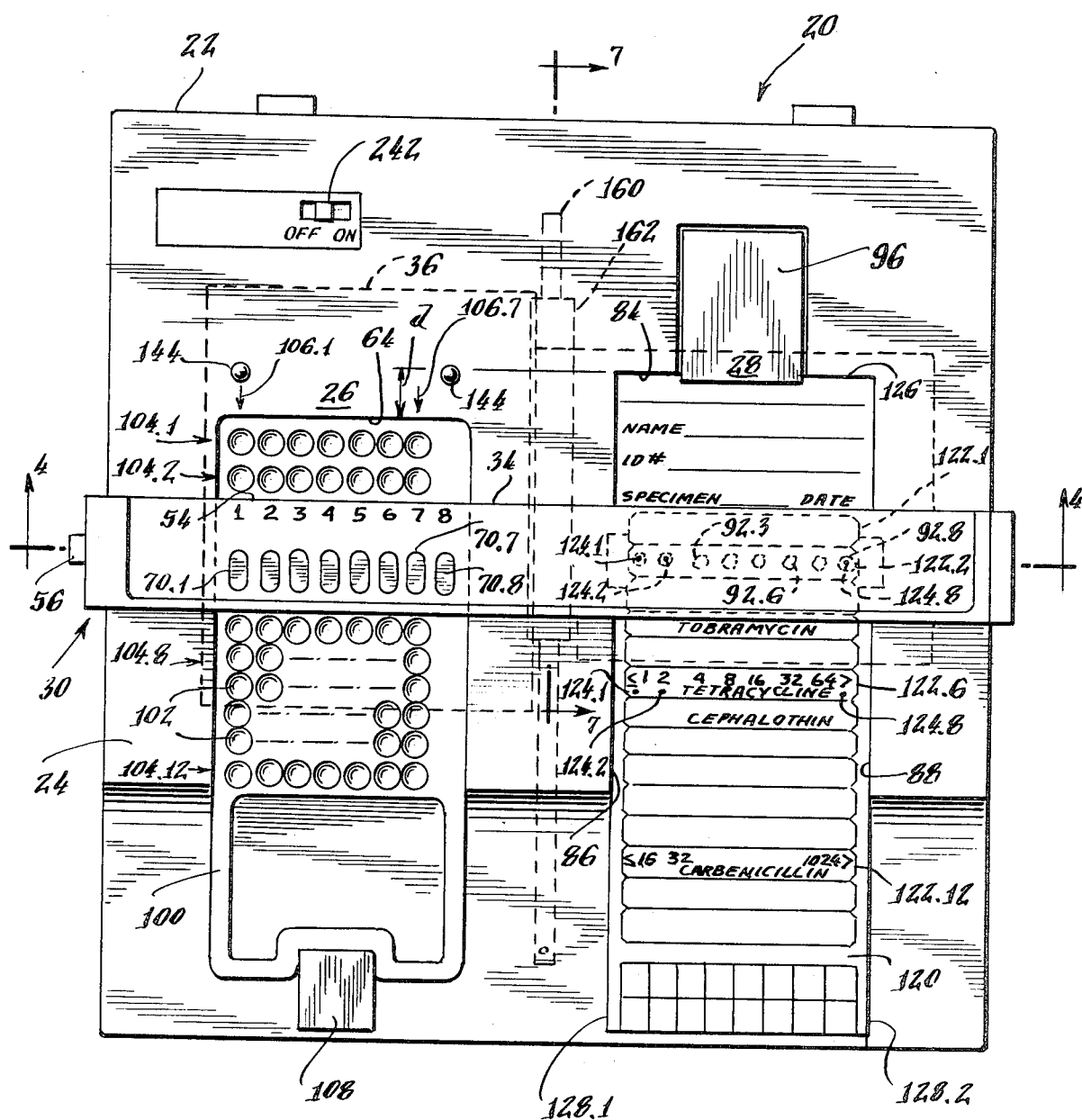
FIG. 2 is a top plan view of an apparatus in accordance with the invention.
Figure 3:
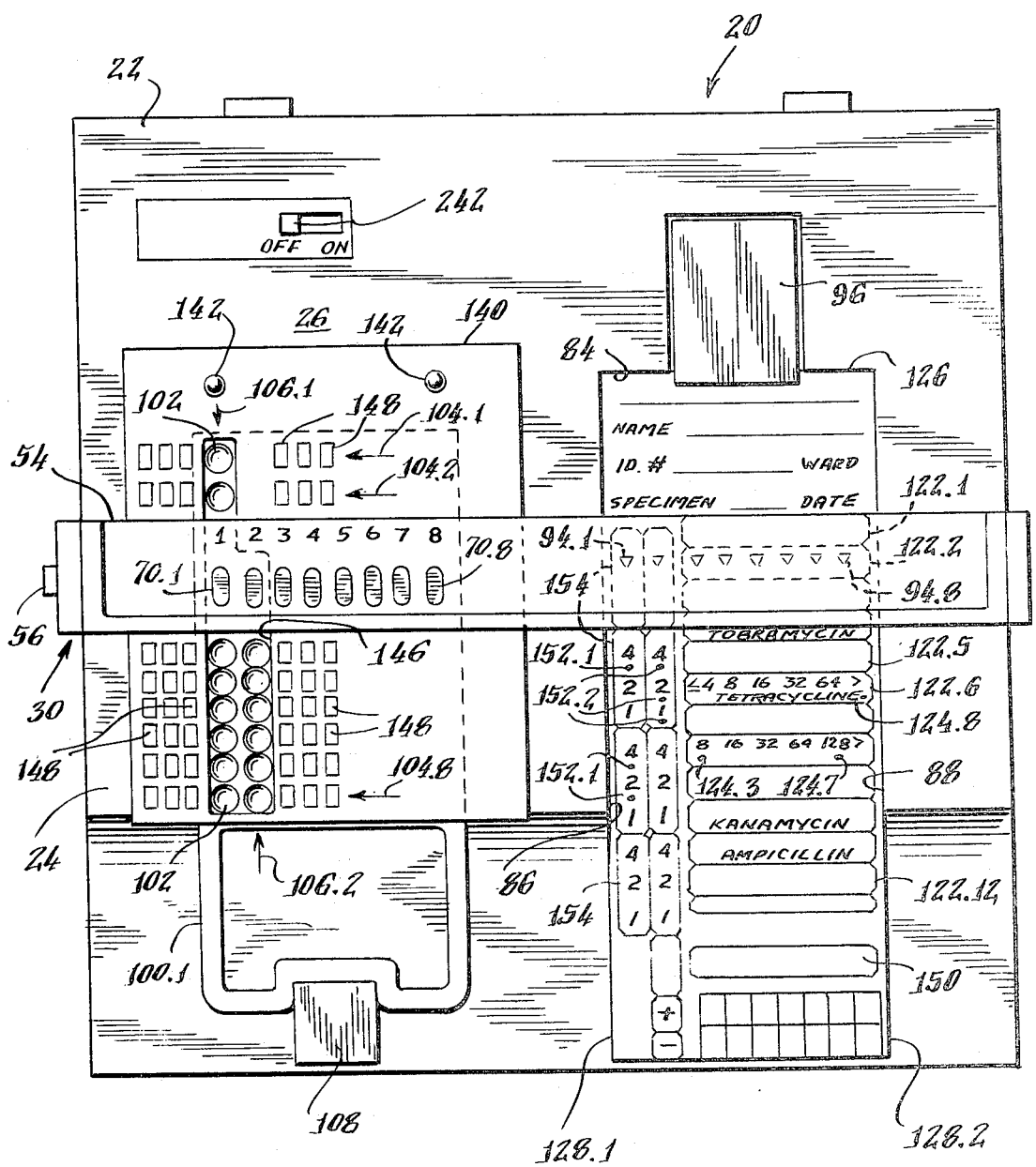
FIG. 3 is another top plan view of an apparatus in accordance with the invention.

In the embodiment of FIG. 3, the apparatus 20 is employed to analyze a tray 100.1 containing an arrangement of microbiological tests different from those employed in the tray 100 in FIG. 2. Tray 100.1 has the first two columns 106.1 and 106.2 of test wells 102 filled with compounds which, in response to certain organisms, develop different colorations. The technician must visually analyze these colors.

Apparatus 20 is particularly well suited in such color analysis by employing a mask overlay 140 with alignment holes 142 sized to receive alignment pins 144 (see FIG. 2) projecting from top surface 24 of housing 22. Mask 140 is provided with a transparent aperture 146, in the form of a cut-out, located to reveal test well columns 106.1 and 106.2 of the underlying tray 100.1. In the particular embodiment of FIG. 3, the aperture 146 is shaped to reveal only certain test wells in the columns as shown. The mask 140 rests on top surface 24 but is located below the arm 30 which is free to move over the mask 140.

Since the revealed test wells 102 are examined as to color, mask 140 is provided adjacent the test wells with appropriately colored markings 148 to aid the technician in identifying the well having a similar color, depending upon the test being made in the well. This is particularly effective in aiding the technician in making a visual color comparison analysis. The proximity of the color markings 148 to the revealed test wells facilitates these comparisons. The visual alignment of the switches 70 with a well in the columns 106.1 and 106.2 further assures appropriate marking of a score form 150 located in the test scoring section 28.

The mask 140 is shown with a single transparent aperture; however, mask 140 may be provided with a plurality of apertures arranged to overly the appropriate test wells while the color markings 148 are closely spaced to the respective apertures. The color markings 148 may take such shape as appears to be visually effective in aiding the technician's color analysis.

Score form 150 has the same width and rows 122 of score value locations as score form 120 in FIG. 2 so that score notations can be made with the recording elements 92 (see FIG. 2). In the view of FIG. 3, only the anvils 94 are being shown in dashed lines. The score forms 120, 150 need not have the same length; however, the first row 122.1 of score values should be spaced the proper distance from edge 126 to assure correct registration with rows 104 in the tray 100.1.

Color valuations are recorded on score form 150 with a score value location such as denoted at 152 within vertically oriented line enclosed segments 154. These score value segments 154 are used to aid in the identification of the organisms in the test wells 102. The score form 150 thus enables the recording of test well valuations which enable both an identification of the organism and the minimum inhibitory count (MIC) as with form 120.

Since a color comparison usually requires a different background color for analyzing the test wells 102, the shutter assembly lever 56 may, as appears necessary, be adjusted to a mixed background position relative to arm 30 as shown in FIG. 3.

FIGS. 4 and 5 illustrate the alignment and construction features of the housing 22 and arm 30 with greater detail. These figures are section views of FIG. 2, but for purposes of clarity a mask 140 as shown and described with reference to FIG. 3 is shown in position.

The arm 30 is in the form of a closed loop structure with its upper segment 34 above the top surface 24 of housing 22 and the lower segment 36 below top surface 24 inside the housing. The arm moves on a centrally located shaft 160, which is attached to housing 22, with suitable linear bearings 162 (only one being visible in FIG. 5). Nylon set screws such as 164 are used at the sides of lower segment 36 to slide on shoulders 168 of housing 22 and maintain the arm 30 level.

The lower segment 30 supports the test well illuminating and shutter assembly 50 below the test analysis section 26, the recording element 92 below the test scoring section 28 and associated electronic drive circuits 170 for the recording elements 92.

Test well illumination is obtained with an elongate light source 172 formed in a U-shape and supported on a bracket 174 with spring elements 176. Light source 172 is a fluorescent light for which a conventional ballast (not shown) is also provided. The elongate light source 172 enables a uniform distribution of light along slot 52 in a shutter assembly 178 to illuminate each row 104 of test wells from the bottom.

The light from light source 172 is passed through a light diffuser plate 180 attached to the shutter assembly 178 and spaced therefrom with spacers 182. The diffuser 180 provides a colored background, such as white. The light source 172 is so located to provide the desired light spectrum, such as an approximation of daylight. The shutter assembly 178 includes separate shutters 184, 186 attached to an aperture plate 188 as more particularly shown and described with reference to FIGS. 10-12. The aperture plate 188 has the test well illuminating slot 52 and is so positioned relative to reference edge 54 on arm 30 that a technician may view a row of test wells against either a light or dark background when looking vertically down along arrow 190.

The up-turned edges 192, 194 (see FIG. 10) along slot 52 are formed in aperture plate 188 and reduce light from source 172 from reaching those test well rows 104 which are not in alignment with reference edge 54. Background illumination control is obtained by interposing one or both of the shutters 184, 186 in slot 52.

In the view of FIG. 5, the shutter 186 is shown moved to a light interrupting position corresponding to the mixed position of the shutter lever 56 as shown in FIGS. 1 and 2. With this position of shutter 186, a dark background is presented to a technician looking straight down along the direction of arrow 190. Yet, the shutter 186 but partially blocks slot and leaves a narrow elongated aperture 191, not visible to the technician because of the shielding effect of the inclined edge 194. Light from lamp 172 may pass through aperture 191 to illuminate the test wells, yet a dark background is provided for the visual analysis. The light angle through aperture 191 is selected to enhance readability of the wells.

As illustrated in FIG. 4 and in greater detail in FIG. 6, the test scoring section 28 includes an array of electrically driven recording elements 92.1–92.8 in the form of solenoids, each of which operates to drive a hammer plunger 193 through a slot 90 against a score form such as 120. In alignment with the travel path of a hammer plunger 193 is an anvil 94 located on the other side of score form 120 and attached to the upper segment of arm 30. The top surfaces of the hammer plungers 193 are flat while the anvils are embossed with a symbol such as an arrow or other mark for pointing to a score value on the score form 120. The solenoid recording elements 92 are mounted to a bracket 195 attached to the lower segment 36 of arm 30 while electrically coupled with connectors to a circuit board (not shown) on which the drive circuits for the recording solenoids are located. The circuit board is also mounted to lower segment 36 of arm 30 and includes suitable drive circuits as are well known to activate recording solenoids 92.

FIG. 7 illustrates a detent mechanism 130 with which arm 30 is provided with discrete incremental index positions whereby reference edge 54 can be easily aligned with a row 104 of test wells 102. A rack 196 is shown connected to top surface wall 48 of housing 22 with suitable brackets 198. The rack 196 has a plurality of detents 200 along a lower edge 202. The rack 196 is so positioned that each detent 200 is in predetermined alignment with a row 104 of test wells 102 of a tray 100 placed in the test section 26.

In contact with rack 196 is a roller 204 mounted on a spring element 206 which biases the roller 204 to ride in and out of detents 200. Spring element 206 is mounted on a bracket 208 connected to lower segment 36 of arm 30. Hence, as arm 30 is moved along shaft 160, arm 30 has successive stable index positions to facilitate alignment of the arm 30 over the test analysis section 26. Suitable stops (not shown) are provided to limit movement of arm 30 along shaft 160 and prevent disconnection of roller 204 from rack 192.

Figure 9:
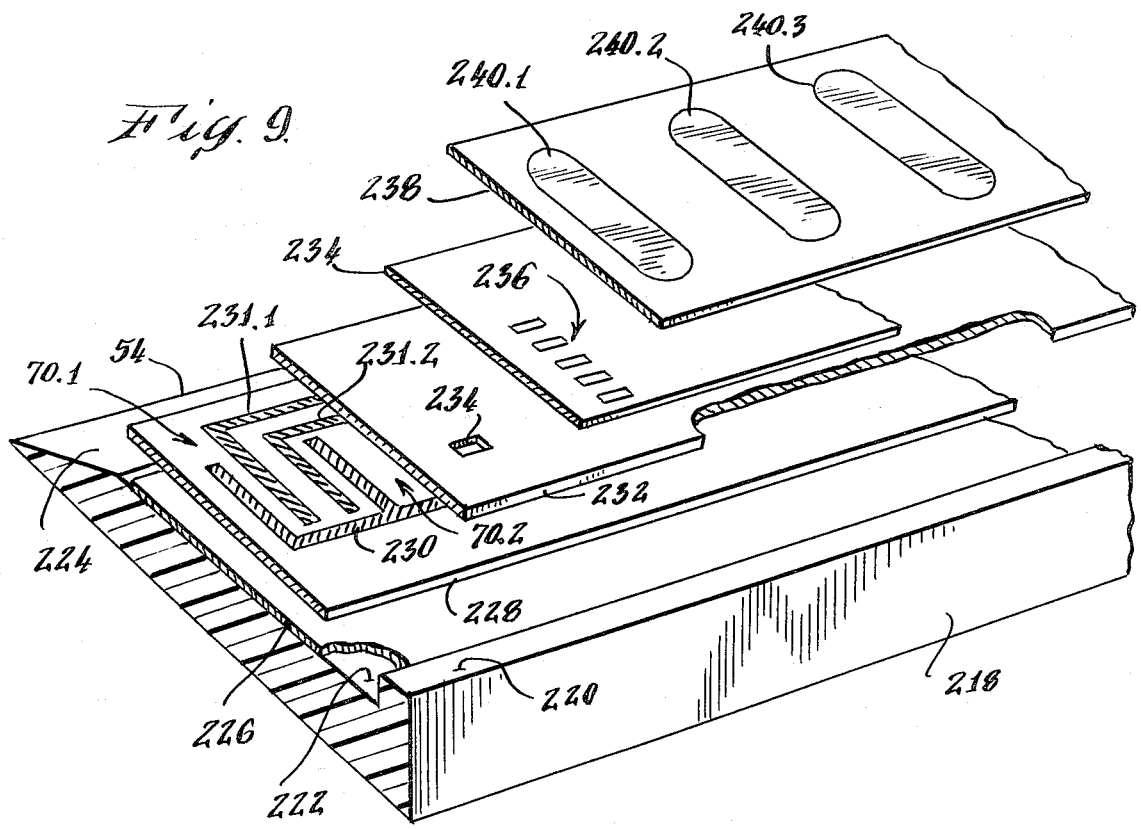
FIG. 9 is an exploded partial perspective view of the upper arm segment shown in FIG. 8.

With reference to FIGS. 8 and 9 and as previously mentioned, arm 30 carries score signal generators 70.1–70.8 which preferably are formed of membrane switches. These form a relatively flat profile on the top of arm segment 34 yet with good tactile feel for the technician. The upper arm segment 34 is shaped with a rigid metal bar 218 having a raised back edge 220, a flat surface 222 and a tapered front 224 leading to reference edge 54.

A double adhesive layer 226 is placed on surface 222 and a conductor strip 228 carrying a common conductor 230 and actuating conductors 231 is placed over layer 226. A thin spacer 232 with strips of double backed adhesive on both sides (but not shown) having a plurality of apertures 234 in alignment with switch positions 70.1-70.8 is then placed on top of strip 228. A second conductor strip 234 carrying a plurality of separate conductors, aligned such as 236, is then located over spacer 232. A conductor such as 236 faces spacer 232 to make contact with the common conductor 230 through aperture 234 when depressed. A cover 238 carrying a strip of double backed adhesive material is placed over strip 234. Cover 238 carries suitable printing legends 240 to denote the location of switches 70 as well as numerical characters as shown in FIG. 8.

Electrical energization of switches 70.1-70.4 is obtained from suitable electrical circuit boards inside housing 22. Such energization may simply mean a connection of, for example, the common conductor 230 to ground or to some other potential while the other conductor 236 is connected in a circuit leading to activate a recording solenoid 92 or another recording device. The electrical connection of score signal generating switches 70.1-70.8 is made in such manner that no wiring is visible from outside of housing 22. This is accomplished by leading the electrical conductor strips to a side end of the upper arm segment 34 and thence through an opening in the arm to the lower segment 36 for electrical connection to the recording solenoid drive circuits.

Housing 22 includes a suitable conventional stationary power supply and a.c. source (not shown) to deliver power as it is needed for the test well illuminating lamp 172 and drive circuits for the recording solenoids 92. Electrical connection between the supply and the movable power requiring circuit elements on arm 30 is with flexible electric wires located to avoid excessive bending and interference with mechanical components. An on/off power switch 242 is located at top surface 24 as shown in FIGS. 1-3.

Figure 10:
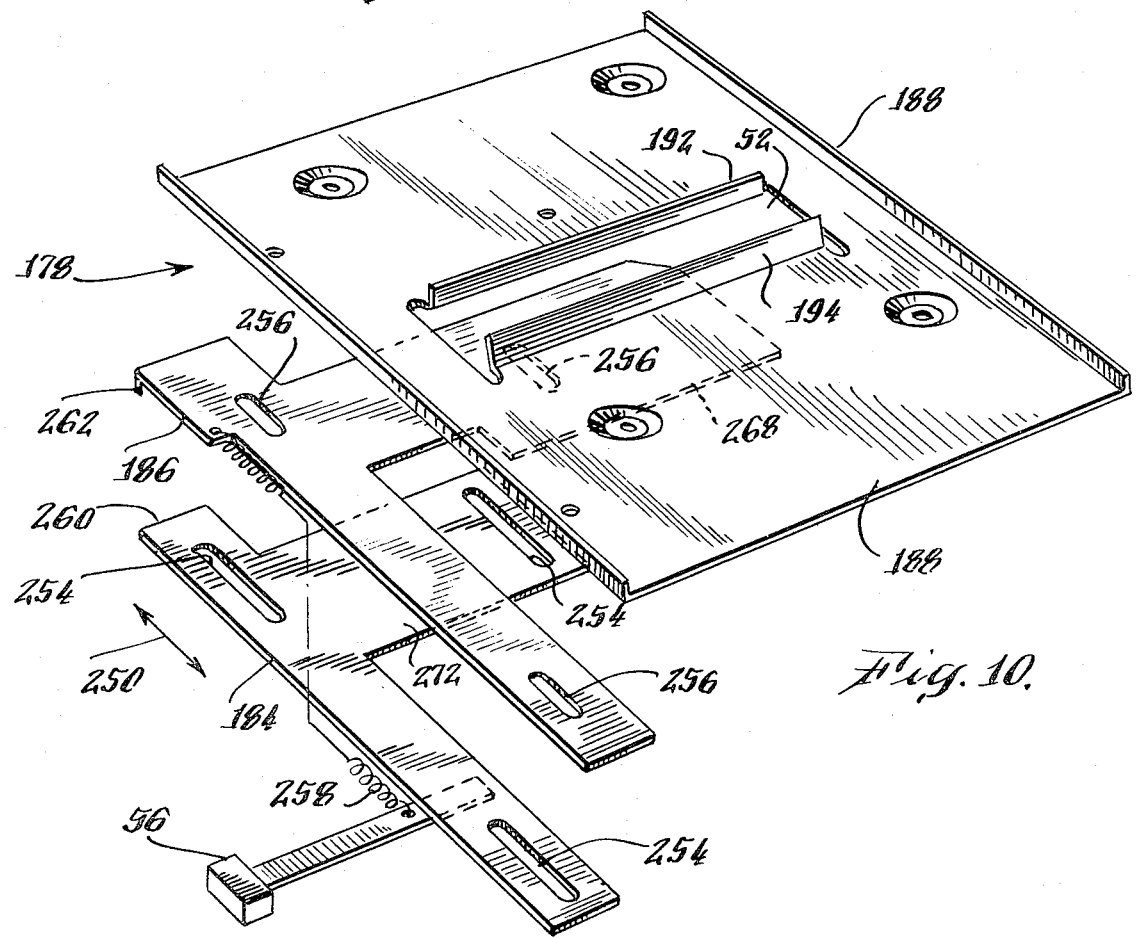
FIG. 10 is an exploded perspective view of a shutter assembly employed in the apparatus of FIG. 2.

FIGS. 10-12 illustrate the shutter assembly without the light diffuser plate 180 as shown in FIG. 5. The shutters 184, 186 are in the form of plates and are mounted to aperture plate 188 for movement in the directions indicated by doubleheaded arrow 250. Sliding movement is controlled by pins 252 located through sets of slots 254, 256 in plates 184 and 186 respectively. Plates 184, 186 are connected by a tension spring 258 which urges edge 260 of plate 184 to seat against bent-over lip 262 of shutter plate 186.

Hence, in one position of shutter control lever 56, as shown in FIGS. 4 and 5 and in dotted outline at 264 in FIG. 11, the shutter plates 184, 186 are withdrawn and slot 52 is unobstructed. When the lever arm 56 is moved to the intermediate position as shown at 266 in FIG. 11, the action of spring 258 causes both plates 184, 186 to move together. However, initially only shutter segment 268 of plate 186 is moved to partially obstruct slot 52 and present a dark background for the test wells overlying the segment 268 while still allowing light from lamp 172 to pass through a narrow aperture as previously explained. This condition coincides with the contact of pins 252 with the ends of shorter slots 256 in plate 186.

This type of mixed background illumination is normally suitable when both organism identification and minimum inhibitory counts are to be scored as described with reference to FIG. 3.

When the lever 56 is further moved in the direction indicated by arrow 270 in FIG. 12, the pins 252 prevent further movement of plate 186 but enable plate 184 to be moved until pins 252 engage the ends of slots 254 at which position segment 272 of shutter plate 184 completes obstruction of slot 52. In both instances, the shutters 184, 186 do not completely close off slot 52 and thus permit light to come through, though shielded by inclined edge 194, at an angle onto the row of test wells in alignment with slot 52. Hence, these wells can be observed against a black background with illumination still being applied.

The housing 22 is formed of separate upper and lower castings which are suitably connected together. Similarly, the arm 30 and its upper and lower segments 34, 36 are formed of rigid castings to maintain structural integrity and alignments as described.

Having thus described an apparatus in accordance with the invention for analyzing and evaluating tests in a plurality of wells in a tray, the advantages of the invention can be appreciated. The apparatus is formed to visually aid a technician and enable him in a semiautomatic manner to visually analyze the test wells and accurately evaluate his analysis in a rapid procedure. Variations from the described embodiment may be made by one skilled in the art without departing from the scope of the invention.

What is claimed is:

1. An apparatus for analyzing and evaluating tests made in a plurality of wells located in a pattern of rows on a tray comprising:

a housing having a top surface defining a test analysis section shaped to receive a said tray;

an arm mounted to the housing and extending over said housing top surface, said arm being movable relative to and over said test analysis section, said arm having a reference edge for alignment with rows of wells in a tray placed in the test analysis section;

a plurality of manually actuated signal generators mounted on said arm and located thereon to move over the test analysis section, and with said plurality of signal generators being respectively located for visual registration with a different well in a row of wells in a tray when placed in said test analysis section, whereby when said arm is moved across said housing top surface with said reference edge in successive registration with a row of wells, said signals may accurately and conveniently represent an evaluation of the tests in the wells of a tray.

2. An apparatus as set forth in claim 1 wherein said arm further includes:

an upper segment having said reference edge and carrying said signal generators at predetermined spaced intervals over said test analysis section; and a lower segment supporting said upper segment and located inside said housing for movement in a direction enabling said reference edge to become aligned with successive predetermined positions over said test analysis section.

3. An apparatus as set forth in claim 2 and further including:

means mounted to said lower segment for producing a slot of light aligned parallel with and located lower than said reference edge to illuminate the bottom of a row of test wells in a tray when placed in said test analysis section.

4. An apparatus as set forth in claim 3 wherein said slot of light producing means includes an elongate fluorescent light source and a light diffuser plate mounted adjacent to and over the light source.

5. An apparatus as set forth in claim 3 wherein said slot of light producing means further includes:
shutter means mounted to said lower segment for selectively masking said slot of light.

6. An apparatus as set forth in claim 5 wherein said shutter means includes:
first and second shutter plates slidingly mounted to said lower segment, each of said shutter plates having a masking segment sized and located to partially mask selected portions of said slot of light to provide a darkened background for visual analysis of test wells below which said mask segments are located.

7. An apparatus as set forth in claim 7 wherein said shutter means further includes:
means mounted to said upper housing segment for maintaining said first and second shutter plates slidingly adjacent each other and enable them to move between different partial slot masking and retracted positions;
spring means operative between the first and second shutter plates to normally bias them to move together under control by said first shutter plate while enabling said first plate to be individually moved to its partial slot masking position.

8. An apparatus as set forth in claim 7 wherein said means for maintaining said first and second shutter plates slidingly adjacent each other further includes:
a plurality of aligned pairs of first and second slots respectively in said first and second shutter plates with a retaining pin extending through each aligned pair of slots;
said slots being sized to enable said first and second shutter plates to move between their respective slot masking and retracted positions;
said first slots being longer than said second slots to enable said first shutter plate to be individually moved to and away from its slot masking position.

9. An apparatus as set forth in claim 1 wherein said score signal generators are a plurality of switches which are manually actuatable from the top of said arm.

10. An apparatus for analyzing and evaluating tests made in a plurality of wells located in a pattern of rows on a tray comprising:
a housing having a top surface defining a tray analysis section and a test scoring section, with said tray analysis section being shaped to receive said tray and said test scoring section being shaped to receive a score form having score value locations in corresponding spatial relationship with the location of wells on a tray;
an arm mounted to the housing and extending over said housing top surface, said arm being movable relative to the top surface and over both said tray analysis section and said test scoring section, said arm having a reference edge for alignment with positions along the tray analysis section in correspondence with rows of wells of a said tray placed in the tray analysis section;
means on said housing for locating said tray and score form in a predetermined relationship with each other so that when said arm reference edge is aligned with one of said positons said arm is also operatively disposed over a corresponding row of score value locations of a score form placed in said test scoring section;
score signal generating means mounted on said arm and located to move over the tray analysis section in visual registration with wells in a tray for generating score signals individually associated with a well in a row of wells in a tray; and
means mounted to said arm and located thereon to move relative to the test scoring section for recording, in response to said score signals, notations on a said score form at score value locations corresponding to the wells in a row which is in alignment with said reference edge, whereby when said arm is moved across said housing upper surface an evaluation of the tests in the wells of a tray can be accurately and conveniently formed on said score form.

11. An apparatus as set forth in claim 10 and further including
a score form for use in the test scoring section of the housing, said score form having said score value locations in corresponding spatial relationship with the locations of wells on a tray.

12. An apparatus as set forth in claim 11 wherein said locating means includes reference walls in said tray analysis and test scoring sections and spaced relative to each other as measured along the direction of movement of the arm located such as to place a said tray and score form with said predetermined spatial relationship; and
wherein said score form has a reference edge located to seat against a reference surface in the test scoring section, the score value locations on a score form being arranged in successive rows with like spacing as between successive rows of wells on a said tray;
said score value locations further being so spaced from the reference edge of the score form that when a row of wells is aligned with said arm reference edge, said recording means is operatively located with respect to a corresponding row of score value locations.

13. An apparatus as set forth in claim 10 and further including
a mask sized to overly said tray analysis section, said mask having a transparent segment shaped to visually reveal predetermined underlying wells of a tray.

14. An apparatus as set forth in claim 13 wherein said score form is provided with line enclosed segments enclosing score value locations corresponding to wells revealed by the transparent section of said mask.

15. An apparatus as set forth in claims 13 or 14 wherein said mask is provided with color indications in mask areas adjacent said wells revealed by the transparent segment to aid in visual color identification of tests in said latter wells.

16. An apparatus as set forth in claim 14 and further including
means mounted to move with said arm and located inside the housing below said top surface for illuminating a group of wells corresponding to score value locations within a said line enclosed segment on said score form.

17. An apparatus as set forth in claim 10 and further including
means mounted to move with said arm and located inside the housing below said top surface for illuminating the underside of a selected group of said wells in a said tray.

18. An apparatus as set forth in claim 17 wherein said illuminating means illuminates an elongate slot transverse to the direction of motion of the arm and parallel to the reference edge of said arm.

19. An apparatus as set forth in claims 17, 18 or 16 wherein said illuminating means further comprises:
means for selectively placing a light or dark background below said group of wells.

20. An apparatus as set forth in claim 10 and further including
means for providing said arm with successive stable index positions in alignment with said rows of wells in a said tray.

21. An apparatus as set forth in claim 10 wherein said score signal generating means comprises a row of switches respectively in registration with a well in a row of wells on a said tray.

22. An apparatus as set forth in claim 10 or 21 wherein said recording means comprises a row of solenoids and anvils, respectively located below and above said top surface and on said arm, each solenoid having a hammer plunger aligned to move against an anvil.

23. An apparatus for analyzing and evaluating microbiological tests made in a plurality of wells located in a pattern of rows on a tray comprising:
a score form having score value locations in corresponding spatial relationship with locations of wells on a tray;
a housing having a top surface defining a tray analysis section and a test scoring section alongside therewith, said tray analysis section and said test scoring section being shaped to respectively receive a tray and said score form so as to place the wells on the tray in predetermined spatial relationship with corresponding score value locations on the score form;
an alignment arm mounted above said housing top surface and being movable relative to and over said tray analysis section and test scoring section, said arm having a reference edge for alignment with rows of wells of a tray placed in the tray analysis section;
means mounted to said arm and located thereon to move over the tray analysis section in visual registration with wells in a tray for generating signals individually associated with a well in a row of wells in a tray;
means mounted to said arm and located thereon to move relative to the scoring section for recording in response to said signal notations on the score form at score value locations corresponding to the wells associated with said signals;
whereby when said arm is moved across said housing top surface, an evaluation of the tests in the wells of a tray can be accurately and conveniently recorded on said score form.

24. An apparatus as set forth in claim 23 and further including:
means mounted to said arm and below the top surface for generating an elongate light region located in front of and parallel to said reference edge of the arm.

25. An apparatus as set forth in claim 24 wherein said light region generating means further includes:
an elongate light source for producing light for said region; and
means for selectively masking a portion of said light region and providing a darkened background at said portion while partially enabling the passage of light from said light source at said portion towards a region in front of said reference edge.

26. An apparatus as set forth in claim 25 wherein said light generating means further comprises:
a light diffuser disposed over said light source.

27. An apparatus as set forth in claim 25 or 26 wherein said masking means further includes:
a plurality of shutter plates located to selectively and partially obstruct said elongate light region and produce said darkened background.

28. An apparatus as set forth in claim 23 wherein said recording means further includes:
a row of anvils having marking embossments thereon and mounted to said arm facing said top surface carrying a score form; and
a row of recording solenoids mounted inside said housing on said arm and having hammer-plungers disposed to strike an anvil,
said top surface having an opening therein to enable said hammer-plungers to move towards said anvils to form marks on the score form at score value locations in correspondence with locations of wells in front of said arm reference edge.

29. An apparatus as set forth in claim 23 wherein said top surface of said housing has first and second recesses respectively at said tray analysis and test scoring sections;
said first recess at said tray analysis section having a bottom and an aperture therein, and bounded by an end wall and a pair of side walls, said side walls being spaced to freely space but accurately locate a tray in said tray analysis section with said wells in registration with the signal generating means mounted on said arm and operative through said aperture in the recess bottom for illuminating a row of tray wells located in front of said reference edge;
said second recess at said test scoring section having a bottom and bounded by an end wall and a pair of side walls, said side walls being spaced to receive said score form, with the relative spacing between the end walls of said first and second recesses, as measured along the direction of motion of said arm, being selected to register the rows of score value locations on the score form with corresponding rows of wells in said tray.

* * * * *